(12) United States Patent
Hua et al.

(10) Patent No.: US 12,350,503 B2
(45) Date of Patent: Jul. 8, 2025

(54) LEADLESS LEFT-BUNDLE-BRANCH PACEMAKER

(71) Applicant: FUWAI HOSPITAL, CAMS & PUMC, Beijing (CN)

(72) Inventors: Wei Hua, Beijing (CN); Min Gu, Beijing (CN); Hongxia Niu, Beijing (CN)

(73) Assignee: FUWAI HOSPITAL, CAMS & PUMC, Beijing (CN)

( * ) Notice: Subject to any disclaimer, the term of this patent is extended or adjusted under 35 U.S.C. 154(b) by 0 days.

(21) Appl. No.: 18/557,809

(22) PCT Filed: Sep. 28, 2022

(86) PCT No.: PCT/CN2022/122126
§ 371 (c)(1),
(2) Date: Oct. 27, 2023

(87) PCT Pub. No.: WO2023/056867
PCT Pub. Date: Apr. 13, 2023

(65) Prior Publication Data
US 2024/0207624 A1 Jun. 27, 2024

(30) Foreign Application Priority Data
Oct. 8, 2021 (CN) .......................... 202122418340.4

(51) Int. Cl.
*A61N 1/37* (2006.01)
*A61N 1/05* (2006.01)
*A61N 1/375* (2006.01)

(52) U.S. Cl.
CPC ......... *A61N 1/3756* (2013.01); *A61N 1/0565* (2013.01); *A61N 1/0573* (2013.01); *A61N 1/37512* (2017.08); *A61N 1/37518* (2017.08)

(58) Field of Classification Search
CPC .......................... A61N 1/3756; A61N 1/37518
See application file for complete search history.

(56) References Cited

U.S. PATENT DOCUMENTS 4,827,940 A * 5/1989 Mayer ...................... A61B 5/29
600/377
4,886,074 A * 12/1989 Bisping ................ A61N 1/0573
607/116

(Continued)

FOREIGN PATENT DOCUMENTS

| CN | 103328040 A | 9/2013 |
| CN | 111246910 A | 6/2020 |

(Continued)

OTHER PUBLICATIONS

International Search Report and Written Opinion of the International Searching Authority mailed on Nov. 30, 2022, for PCT Application No. PCT/CN2022/122126, filed on Sep. 28, 2022, 12 pages (with English Translation).

(Continued)

*Primary Examiner* — Eric D. Bertram
(74) *Attorney, Agent, or Firm* — Cooley LLP

(57) ABSTRACT

The present disclosure belongs to the technical field of artificial cardiac pacemakers, and particularly relates to a leadless left-bundle-branch pacemaker. The leadless left-bundle-branch pacemaker comprises a case and an implant core, wherein the implant core is coaxially arranged inside the case, and a head of the implant core can be rotated out from the inside of the case; the implant core has an implant end that can be rotated out from the inside of the case, and the length of the implant end rotated out from the inside of the case is greater than 10 mm; and an end of the case corresponding to the implant end is provided with a fixing end for fixing the pacemaker.

12 Claims, 3 Drawing Sheets

(56) References Cited

U.S. PATENT DOCUMENTS

| | | | | |
|---|---|---|---|---|
| 4,991,578 | A * | 2/1991 | Cohen | A61M 25/01 607/2 |
| 5,353,800 | A * | 10/1994 | Pohndorf | A61N 1/0573 600/561 |
| 5,447,533 | A * | 9/1995 | Vachon | A61N 1/056 600/374 |
| 5,522,876 | A * | 6/1996 | Rusink | A61N 1/0573 607/128 |
| 5,531,783 | A * | 7/1996 | Giele | A61N 1/0573 600/375 |
| 5,658,326 | A * | 8/1997 | Barsne | A61N 1/0573 607/126 |
| 5,964,795 | A * | 10/1999 | McVenes | A61N 1/056 607/122 |
| 6,091,978 | A * | 7/2000 | Johnson | A61N 1/0568 600/375 |
| 6,408,214 | B1 * | 6/2002 | Williams | A61M 25/0041 607/122 |
| 6,419,868 | B1 * | 7/2002 | Johnson | A61N 1/0573 264/249 |
| 6,931,286 | B2 * | 8/2005 | Sigg | A61M 25/0084 607/126 |
| 6,988,007 | B1 * | 1/2006 | Morgan | A61N 1/056 600/374 |
| 7,044,934 | B2 * | 5/2006 | Mickley | A61M 25/0041 604/164.01 |
| 7,082,335 | B2 * | 7/2006 | Klein | A61N 1/056 607/126 |
| 7,191,015 | B2 * | 3/2007 | Lamson | A61N 1/056 607/129 |
| 7,386,351 | B2 * | 6/2008 | Hine | A61N 1/056 607/122 |
| 7,496,410 | B2 * | 2/2009 | Heil, Jr. | A61N 1/059 607/126 |
| 11,045,653 | B1 | 6/2021 | Makharinsky et al. | |
| 11,253,699 | B1 * | 2/2022 | Williams | A61N 1/0573 |
| 11,446,486 | B1 * | 9/2022 | Dandamudi | A61N 1/0573 |
| 2002/0165442 | A1 * | 11/2002 | Heil, Jr. | A61N 1/0573 600/375 |
| 2003/0023296 | A1 * | 1/2003 | Osypka | A61N 1/056 607/122 |
| 2004/0064158 | A1 * | 4/2004 | Klein | A61N 1/056 607/9 |
| 2006/0206153 | A1 * | 9/2006 | Libbus | A61N 1/3627 607/9 |
| 2010/0305670 | A1 * | 12/2010 | Hall | A61N 1/3752 29/879 |
| 2012/0004714 | A1 * | 1/2012 | Kleve | A61N 1/0563 607/116 |
| 2014/0046389 | A1 * | 2/2014 | Anderson | A61N 1/3684 607/4 |
| 2014/0067036 | A1 * | 3/2014 | Shuros | A61N 1/0573 606/129 |
| 2016/0051823 | A1 | 2/2016 | Maile et al. | |
| 2018/0050208 | A1 * | 2/2018 | Shuros | A61N 1/36843 |
| 2019/0022379 | A1 * | 1/2019 | Foster | A61N 1/375 |
| 2019/0321625 | A1 * | 10/2019 | Shuros | A61N 1/0573 |
| 2020/0114146 | A1 * | 4/2020 | Foster | A61N 1/059 |
| 2020/0230396 | A1 * | 7/2020 | Makharinsky | A61N 1/37512 |
| 2020/0261734 | A1 * | 8/2020 | Yang | A61N 1/0573 |
| 2020/0289835 | A1 * | 9/2020 | Eby | A61N 1/37512 |
| 2022/0362546 | A1 * | 11/2022 | Doerr | A61N 1/0573 |
| 2023/0144919 | A1 * | 5/2023 | Erlebacher | A61M 25/01 607/9 |
| 2024/0009468 | A1 * | 1/2024 | Bauer | A61N 1/3756 |

FOREIGN PATENT DOCUMENTS

| | | |
|---|---|---|
| CN | 111437512 A | 7/2020 |
| CN | 112274777 A | 1/2021 |
| CN | 212730725 U | 3/2021 |
| CN | 214158287 U | 9/2021 |
| CN | 216456543 U | 5/2022 |
| WO | WO-2021083792 A1 | 5/2021 |
| WO | WO-2023056867 A1 | 4/2023 |

OTHER PUBLICATIONS

Extended European Search Report mailed on Aug. 12, 2024, for EP Application No. 22877886.6, filed on Sep. 28, 2022, 8 pages.
Intention to Grant for European Application No. 22877886.6, by Fuwai Hospital, CAMS & PUMC, mailed Nov. 5, 2024; 23 pages.

* cited by examiner

LEADLESS LEFT-BUNDLE-BRANCH PACEMAKER

CROSS-REFERENCE TO RELATED APPLICATIONS

The present application is a National Stage of International Application No. PCT/CN2022/122126 filed on Sep. 28, 2022, which claims the priority of the Chinese patent application No. 202122418340.4, entitled "LEADLESS LEFT-BUNDLE-BRANCH PACEMAKER" and filed on Oct. 8, 2021, both of which are incorporated herein by reference in their entireties.

TECHNICAL FIELD

The present disclosure belongs to the technical field of artificial cardiac pacemakers, and particularly relates to a leadless left-bundle-branch pacemaker.

BACKGROUND

A permanent cardiac pacemaker is an electronic therapeutic instrument implanted in the body. It emits electrical pulses through a pulse generator to stimulate the myocardium in contact with electrodes, causing the myocardium to excite and contract, thereby achieving the purpose of treating bradycardia or heart failure and other diseases. However, leads on traditional pacemakers may have hidden dangers such as dislocation, damage, and systemic infection, and may also cause related complications such as thrombosis, tricuspid regurgitation, pocket infection, and hematoma.

Leadless pacemakers that have emerged in recent years avoid lead-related complications. However, the leadless pacemakers currently used in clinic only contact the myocardial tissue of the right ventricle and can only pace the right ventricle but cannot pace the conductive bundle, so physiological pacing cannot be achieved. Long-term right ventricular pacing changes the normal ventricular activation sequence and artificially causes left bundle branch block in the patient. Long-term right ventricular pacing will increase the patient's risk of long-term heart failure and atrial fibrillation, which is extremely detrimental to patients with cardiac dysfunction who have atrioventricular block and a high percentage of pacing.

SUMMARY

In order to achieve the above objective, the main technical solution adopted in the present disclosure includes the following:

The present disclosure provides a leadless left-bundle-branch pacemaker, including a case and an implant core, wherein the implant core is coaxially arranged inside the case, and a head of the implant core can be rotated out from the inside of the case; the implant core has an implant end that can be rotated out from the inside of the case, and the length of the implant end rotated out from the inside of the case is greater than 10 mm; and an end of the case corresponding to the implant end is provided with a fixing end for fixing the pacemaker.

In some embodiments, both the fixing end and the implant end are spiral-shaped, and the spiral directions of the fixing end and the implant end are consistent.

In some embodiments, the implant core is provided with a first cathode, a second anode, a third anode, and a fourth anode in sequence along an axial direction, and the first cathode is arranged close to the implant end.

In some embodiments, the first cathode, the second anode, the third anode and the fourth anode are equally spaced.

In some embodiments, the fourth anode is located outside the case in a case where the implant end is rotated out to its maximum stroke.

In some embodiments, the case includes an outer wall and an inner wall, a cavity is formed between the outer wall and the inner wall, and a pulse generator for generating electrical pulses is arranged in the cavity.

In some embodiments, the inner wall is provided with an opening, the pulse generator is provided with a first anode, a second cathode, a third cathode, and a fourth cathode, the first anode is electrically connected to the first cathode, the second cathode is electrically connected to the second anode, the third cathode is electrically connected to the third anode, and the fourth cathode is electrically connected to the fourth anode.

In some embodiments, a battery is arranged inside the pulse generator.

In some embodiments, a receiver is arranged in the cavity, and the receiver is electrically connected to the pulse generator.

In some embodiments, the receiver is provided with a receiving module, and the receiving module is configured to receive a remote control signal.

In some embodiments, the head of at least one of the fixing end and the implant end is configured to be tapered.

In some embodiments, the implant end serves as the head and a tail of the implant core is magnetic.

In some embodiments, the tail is provided with a magnetic block.

In some embodiments, the pacemaker has an initial state and a use state. In the initial state, the implant end does not extend beyond the fixing end, and a tail of the implant core extends out of the case. In the use state, the implant end is rotated out from the case and extends beyond the fixing end, and the length of the implant end rotated out is set according to the thickness of a interventricular septum of a patient.

Figure 1:
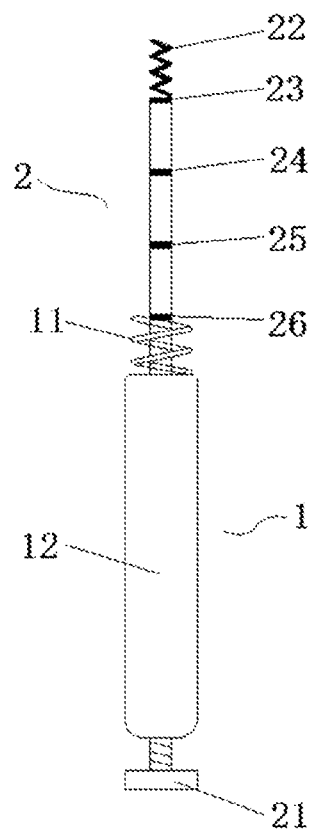
FIG. 1 is a schematic structural diagram of a leadless left-bundle-branch pacemaker according to some embodiments with an implant core completely rotated out.

REFERENCE NUMERALS 1. case; 11. fixing end; 12. outer wall; 13. inner wall; 14. cavity: 15. pulse generator; 151. first anode: 152. second cathode; 153. third cathode; 154. four cathodes; 155. battery: 16. receiver; 161. receiving module;
2. implant core: 21. tail; 22. implant end; 23. first cathode; 24. second anode; 25. third anode; and 26. fourth anode.

DETAILED DESCRIPTION

In order to better understand the above technical solutions, exemplary embodiments of the present disclosure will be described in more detail below with reference to the accompanying drawings. While the exemplary embodiments of the present disclosure are shown in the drawings, it should be understood that the present disclosure may be implemented in various forms and should not be limited to the embodiments set forth herein. Instead, these embodiments are provided so that the present disclosure can be understood more clearly and more thoroughly and the scope of the present disclosure can be fully conveyed to those skilled in the art.

The leadless cardiac pacemaker is a new type of pacemaker that integrates a pulse generator and a pacing electrode. Compared with traditional pacemakers, it does not require intravenous implantation of endocardial leads, subcutaneous incisions and capsular bags. Instead, it is in the form of a microcapsule that is implanted into the patient's heart via a catheter through the femoral vein. The catheter is inserted mainly through the femoral vein of the right leg. The head end of the catheter is connected to a pacemaker. Under the X-ray image, the surgeon adjusts the catheter and places the pacemaker in the appropriate position of the heart.

In order to solve the problems of the prior art, the present disclosure provides a leadless left-bundle-branch pacemaker which can synchronously pace the left ventricle, thus solving the problem of current leadless pacemakers being unable to achieve physiological pacing.

The present disclosure provides a leadless left-bundle-branch pacemaker, including a case and an implant core that is coaxially arranged inside the case, and the implant core can be rotated out from the inside of the case, wherein the implant core has an implant end that can be rotated out from the inside of the case, and the length of the implant end rotated out from the inside of the case is greater than 10 mm; and an end of the case corresponding to the implant end is provided with a fixing end for fixing the pacemaker to the myocardial wall. After the fixing end is fixed to the myocardial wall, the implant core is rotated into the interventricular septum and can be rotated out from the case with different lengths according to the thickness of the interventricular septum of each person, such that the head of the implant core is rotated into the subendocardial left-bundle-branch area of the left ventricle to achieve the purpose of double bundle branch pacing, thereby achieving physiological pacing.

Figure 2:
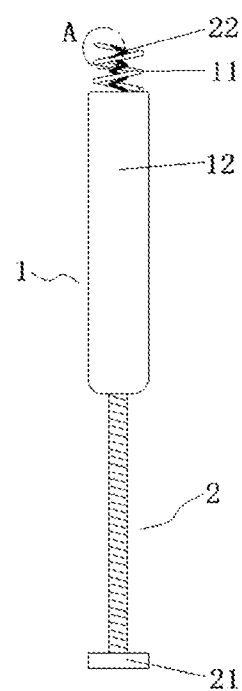
FIG. 2 is a schematic structural diagram of the leadless left-bundle-branch pacemaker according to some embodiments with the implant core not rotated out.
Figure 4:
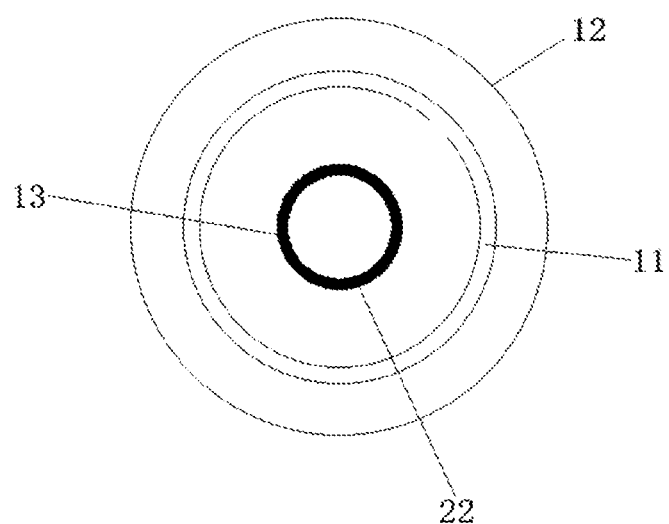
FIG. 4 is a schematic top view of the leadless left-bundle-branch pacemaker according to some embodiments.

As shown in FIGS. 1, 2, and 4, the present disclosure provides a leadless left-bundle-branch pacemaker, including a case 1 and an implant core 2, wherein the implant core 2 is coaxially arranged inside the case 1, and the implant core 2 has a head that can be rotated out from the inside of the case 1. The implant core 2 has an implant end 22 that can be unscrewed from the inside of the case 1. The implant core 2 is in threaded fit with the case 1. The implant end 22 serves as the head and the length of the implant end 22 rotated out from the inside of the case 1 is greater than 10 mm. An end of the case 1 corresponding to the implant end 22 is provided with a fixing end 11 for fixing the pacemaker to the myocardial wall.

After the fixing end 11 of the pacemaker of this embodiment is fixed to the myocardial wall, the implant core 2 is rotated into the interventricular septum and can be rotated out from the case with different lengths according to the thickness of the interventricular septum of each person, such that the head of the implant core 2 is rotated into the subendocardial left-bundle-branch area of the left ventricle to achieve the purpose of double bundle branch pacing, thereby achieving physiological pacing. In this way, it can reduce the patient's risk of long-term heart failure and atrial fibrillation, and is beneficial to patients with cardiac dysfunction who have atrioventricular block and a high proportion of pacing. Moreover, the length of the implant end 22 rotated out from the inside of the case 1 is greater than 10 mm, which can meet the interventricular septal thickness requirements of most patients and reliably reach the subendocardial left-bundle-branch area of the left ventricle, increasing the versatility of the pacemaker.

The pacemaker has an initial state and a use state. As shown in FIG. 2, in the initial state, the implant end 22 does not extend beyond the fixing end 11, and the tail 21 of the implant core 2 can extend out of the case 1. As shown in FIG. 1, in the use state, the implant end 22 of the implant core 2 is rotated out from the case 1 and gradually extends beyond the fixing end 11 until the implant end 22 is rotated out into the subendocardial left-bundle-branch area of the left ventricle. The length of the implant end 22 rotated out is set according to the thickness of the interventricular septum of a person.

In the initial state, the implant end 22 does not extend beyond the fixing end 11, which facilitates the connection of the fixing end 11 to the myocardial wall. If the implant end 22 extends beyond the fixing end 11, the connection between the fixing end 11 and the myocardial wall may be affected. After the case 1 is stably fixed to the myocardial wall, the implant end 22 is rotated out to reach the subendocardial left-bundle-branch area of the left ventricle.

In some embodiments, the implant core 2 has a magnetic tail 21. Optionally, the tail 21 of the implant core 2 is provided with a magnetic block, which can be magnetically attracted to the catheter. In this way, the pacemaker and the catheter can be firmly connected during implantation, and the catheter can smoothly release the pacemaker after implantation. Alternatively, in other embodiments, the tail 21 is connected to a wire. After the pacemaker is implanted, the connection between the tail 21 and the wire is cut off to smoothly release the pacemaker. In this way, interference with the operation of metal components within the pacemaker can be prevented.

In some embodiments, both the fixing end 11 and the implant end 22 are spiral-shaped, and the spiral directions of the fixing end 11 and the implant end 22 are consistent. In this way, the catheter only needs to be driven and rotated in the same direction, which facilitates operation.

Figure 6:
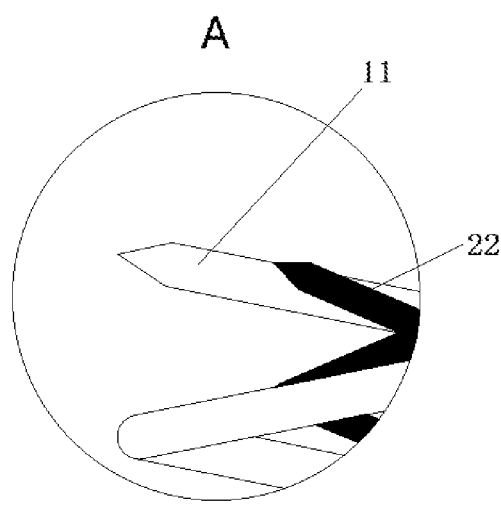
FIG. 6 is an enlarged schematic diagram of Part A in FIG. 2.

Optionally, as shown in FIG. 6, the head of at least one of the fixing end 11 and the implant end 22 is configured to be tapered. The tapered design can also ensure that the pacemaker is rotated into the myocardium more quickly and accurately.

In this embodiment, the leadless left-bundle-branch pacemaker is delivered into the right ventricle of the heart through a catheter. After the fixing end 11 of the pacemaker comes into contact with the myocardium, the fixing end 11 is firmly fixed to the myocardial wall by screwing the catheter, and then the implant core 2 is rotated in. At this time, the length of the implant core 2 rotated in is adjusted according to the thickness of interventricular septum of each person under the X-ray image, until the implant core 2 is rotated into subendocardial left-bundle-branch area of the left ventricle. After the pacemaker is put in place, the catheter is controlled to release the pacemaker and is removed from the body.

Figure 3:
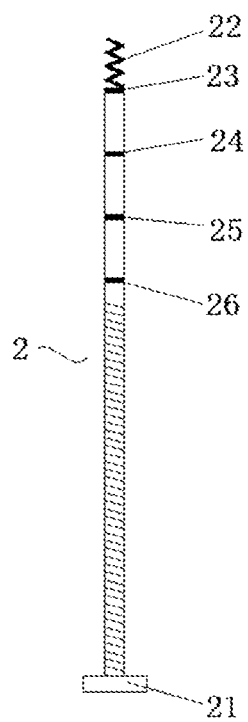
FIG. 3 is a schematic structural diagram of the implant core according to some embodiments.

In some embodiments, as shown in FIGS. 1 and 3, the implant core 2 is provided with a first cathode 23, a second anode 24, a third anode 25 and a fourth anode 26 in sequence along the axial direction, and the first cathode 23 is arranged close to the implant end 22. When the pacemaker is working, the first cathode 23 and one of the anodes on the implant core 2 can be selected to conduct electrical pulses according to the thickness of the interventricular septum of each person, thereby meeting the needs of different patients.

Optionally, the first cathode 23, the second anode 24, the third anode 25 and the fourth anode 26 are equally spaced. In this way, electrodes can be arranged more evenly along the axial direction of the implant core 2, thereby better meeting the electrode connection needs of patients with different interventricular septa.

As shown in FIG. 1, in a case where the implant end 22 is unscrewed to the maximum stroke, the fourth anode 26 is located outside the case 1. When the implant end 22 is unscrewed to the maximum stroke, it can meet the needs of patients with large ventricular septum thickness. In this case, the fourth anode 26 is exposed outside the case 1, and the fourth anode 26 can be selected to meet the electrical pulse conduction needs of patients with large interventricular septum thickness.

Figure 5:
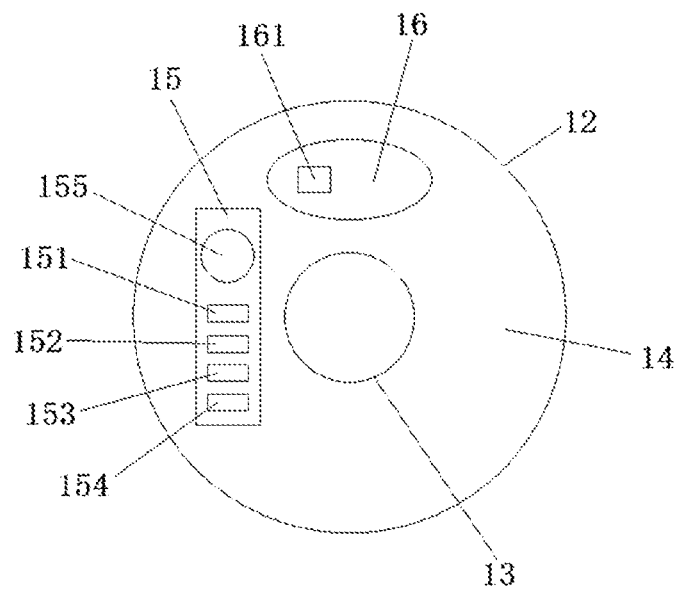
FIG. 5 is a schematic diagram of the internal structure of a case according to some embodiments.

As shown in FIG. 5, the case 1 includes an outer wall 12 and an inner wall 13. A cavity 14 is formed between the outer wall 12 and the inner wall 13. A pulse generator 15 is arranged in the cavity 14 to generate electrical pulses to stimulate the myocardium in contact with the electrodes, causing the myocardium to excite and contract, thereby achieving the purpose of pacing the heart.

The inner wall 13 is provided with an opening. The pulse generator 15 is provided with a first anode 151, a second cathode 152, a third cathode 153, and a fourth cathode 154. Wires are led out from the first anode 151, the second cathode 152, the third cathode 153 and the fourth cathode 154 respectively and pass through the opening, the first anode 151 is electrically connected to the first cathode 23, the second cathode 152 is electrically connected to the second anode 24, the third cathode 153 is electrically connected to the third anode 25, and the fourth cathode 154 is electrically connected to the fourth anode 26. When the pacemaker is working, a suitable pair of electrodes is selected to conduct electrical pulses according to the thickness of the interventricular septum of each person. For example, wires leading from the first cathode 23, the second anode 24, the third anode 25 and the fourth anode 26 may be integrated within the implant core 2.

Specifically, during electrical pulse conduction, the first anode 151 and the first cathode 23 are fixedly selected, and among other three pairs of electrodes, i.e., the second cathode 152 and the second anode 24, the third cathode 153 and the third anode 25, and the fourth cathode 154 and the fourth anode 26, a suitable pair of electrodes is selected through program control according to the thickness of the interventricular septum of each person, so that the first cathode 23 on the implant core 2 is located on one side of the interventricular septum and the anode on the implant core 2 that is selected for use is located on the other side of the interventricular septum.

In some embodiments, a receiver 16 is arranged in the cavity 14, and the receiver 16 is electrically connected to the pulse generator 15. A receiving module 161 is arranged in the receiver 16, and the receiving module 161 can receive a remote control signal from an external pacemaker programmer.

In some embodiments, a battery 155 is also arranged inside the pulse generator 15 to provide power for the pulse generator 15.

In this embodiment, after the pacemaker is placed on the heart, the pacemaker starts to work. At this time, the pacemaker programmer is operated to remotely control the pulse generator 15. First, the receiving module 161 of the receiver 16 receives a remote signal from the program controller, and then transmits the signal to the pulse generator 15. Then, the pulse generator 15 is turned on and connects the anode selected according to the thickness of the interventricular septum. Finally, the pulse generator 15 emits electrical pulses and the electrical pulses are transmitted to the myocardium through wires and electrodes, so that the myocardium contracts after being stimulated by the electrical pulses.

In the description of the present disclosure, it should be understood that the terms "first" and "second" are used for descriptive purposes only but should not be construed as indicating or implying relative importance or implicitly indicating the number of indicated technical features. Therefore, a feature limited by "first" or "second" may explicitly or implicitly include one or more of the features. In the description of the present disclosure, the meaning of "a plurality of" refers to two or more than two, unless otherwise expressly and specifically limited.

In the present disclosure, unless otherwise stated and defined explicitly, the terms such as "install" "link", "connect", and "fix" should be understood in a broad sense. For example, it may be a fixed connection, a detachable connection, or an integrated connection. It may be a mechanical connection or an electrical connection. It may be a direct connection and may also be an indirect connection through an intermediate medium. It may be a communication inside two components or interaction between two components. For those of ordinary skill in the art, the specific meanings of the above terms in the present disclosure can be understood according to specific circumstances.

In the present disclosure, the first feature being "on" or "under" the second feature may mean that the first feature and the second feature are in direct contact or that the first and second features are in indirect contract through an intermediate medium, unless otherwise explicitly stated and defined. Moreover, the first feature being "at the top of", "above" and "on" the second feature may mean that the first feature is right above or diagonally above the second feature, or may merely mean that the first feature is horizontally higher than the second feature. The first feature being "at the bottom of", "below" and "under" the second feature may mean that the first feature is right below or diagonally below the second feature, or may merely mean that the first feature is horizontally lower than the second feature.

As described herein, the description with reference to the terms "an embodiment", "some embodiments", "embodiment", "example", "specific example", "some examples" or the like means specific features, structures, materials or characteristics described in connection with the embodiment or example are included in at least one embodiment or example of the present disclosure. In the present specification, the schematic representation of the above terms is not necessarily directed to the same embodiment or example. Furthermore, the specific features, structures, materials, or characteristics described may be combined in a suitable manner in any one or more embodiments or examples. In addition, those skilled in the art can integrate and combine various embodiments or examples described in the present specification, as well as features of various embodiments or examples, without contradicting each other.

Although the embodiments of the present disclosure have been shown and described, it would be understood that the above-described embodiments are illustrative but should not be construed as limiting the scope of the present disclosure. Changes, modifications, substitutions and variations of the above-described embodiments may be made by those skilled in the art within the scope of the present disclosure.

The invention claimed is:

1. A leadless left-bundle-branch pacemaker, comprising:
a case; and
an implant core coaxially arranged inside the case, wherein a head of the implant core can be rotated out from the inside of the case, the implant core has an implant end configured to be rotated out from the inside of the case, and the length of the implant end rotated out from the inside of the case is greater than 10 mm, the implant end serves as the head, a tail of the implant core is magnetic;
wherein an end of the case corresponding to the implant end is provided with a fixing end for fixing the pacemaker;
wherein the pacemaker has an initial state and a use state; in the initial state, the implant end does not extend beyond the fixing end, and the tail of the implant core extends out of the case; in the use state, the implant end is rotated out from the case and extends beyond the fixing end, and the length of the implant end rotated out is set according to the thickness of a interventricular septum of a person.

2. The leadless left-bundle-branch pacemaker according to claim 1, wherein both the fixing end and the implant end are spiral-shaped, and the spiral directions of the fixing end and the implant end are consistent.

3. The leadless left-bundle-branch pacemaker according to claim 2, wherein the head of at least one of the fixing end and the implant end is configured to be tapered.

4. The leadless left-bundle-branch pacemaker according to claim 1, wherein the implant core is provided with a cathode of a first electrode group, a anode of a second electrode group, a anode of a third electrode group and a anode of a fourth electrode group in sequence along an axial direction, and the first cathode of the first electrode group is arranged close to the implant end.

5. The leadless left-bundle-branch pacemaker according to claim 4, wherein the cathode of the first electrode group, the anode of the second electrode group, the anode of the third electrode group and the fourth anode of the fourth electrode group are equally spaced.

6. The leadless left-bundle-branch pacemaker according to claim 4, wherein the anode of the fourth electrode group is located outside the case in a case where the implant end is rotated out to its maximum stroke.

7. The leadless left-bundle-branch pacemaker according to claim 4, wherein the case comprises an outer wall and an inner wall, a cavity is formed between the outer wall and the inner wall, and a pulse generator for generating electrical pulses is arranged in the cavity.

8. The leadless left-bundle-branch pacemaker according to claim 7, wherein the inner wall is provided with an opening, the pulse generator is provided with a anode of the first electrode group, a cathode of the second electrode group, a cathode of the third electrode group and a cathode of the fourth electrode group, the anode of the first electrode group is electrically connected to the cathode of the first electrode group, the cathode of the second electrode group is electrically connected to the anode of the second electrode group, the cathode of the third electrical group is electrically connected to the anode of the third electrical group, and the cathode of the fourth electrode group is electrically connected to the anode of the fourth electrode group.

9. The leadless left-bundle-branch pacemaker according to claim 7, wherein a battery is arranged inside the pulse generator.

10. The leadless left-bundle-branch pacemaker according to claim 7, wherein a receiver is arranged in the cavity, and the receiver is electrically connected to the pulse generator.

11. The leadless left-bundle-branch pacemaker according to claim 10, wherein the receiver is provided with a receiving module, and the receiving module is configured to receive a remote control signal.

12. The leadless left-bundle-branch pacemaker according to claim 1, wherein the tail is provided with a magnetic block.

* * * * *